United States Patent
Ellman et al.

(10) Patent No.: US 6,346,078 B1
(45) Date of Patent: Feb. 12, 2002

(54) EYELID RETRACTOR FOR ELECTROSURGERY

(76) Inventors: Alan G. Ellman; Jon C. Garito, both of 1135 Railroad Ave., Hewlett, NY (US) 11557

(*) Notice: Subject to any disclaimer, the term of this patent is extended or adjusted under 35 U.S.C. 154(b) by 0 days.

(21) Appl. No.: 09/728,384

(22) Filed: Dec. 4, 2000

(51) Int. Cl.[7] .............................................. A61B 17/02
(52) U.S. Cl. ...................... 600/235; 600/214; 600/236
(58) Field of Search ................................ 600/235, 236, 600/217, 210, 213, 219, 214

(56) References Cited

U.S. PATENT DOCUMENTS

| | | | | |
|---|---|---|---|---|
| 605,715 A | * | 6/1898 | Hohmann ................... 600/235 |
| 1,400,616 A | * | 12/1921 | McCrory et al. ........... 600/217 |
| 2,863,444 A | * | 12/1958 | Winsten ..................... 600/214 |
| 3,542,015 A | * | 11/1970 | Steinman ................... 600/217 |
| 3,857,386 A | * | 12/1974 | Ashbell ...................... 600/217 |
| 5,174,279 A | * | 12/1992 | Cobo et al. ................. 600/236 |
| 5,213,114 A | * | 5/1993 | Bailey, Jr. .................. 600/236 |
| 5,334,194 A | * | 8/1994 | Mikhail ...................... 600/217 |
| 5,352,220 A | * | 10/1994 | Abidin et al. ............... 600/219 |
| 5,769,781 A | * | 6/1998 | Chappuis .................... 600/235 |
| 5,785,649 A | * | 7/1998 | Fowler, Jr. .................. 600/217 |
| 5,876,333 A | * | 3/1999 | Bigliani et al. ............. 600/235 |
| 5,964,699 A | * | 10/1999 | Rullo et al. ................. 600/217 |

FOREIGN PATENT DOCUMENTS

GB      17376     * 10/1893                 600/217

* cited by examiner

Primary Examiner—Paul J. Hirsch

(57) ABSTRACT

A lid retractor for use, for example, in transconjuntival blepharoplasty electrosurgery on eyelids which avoids having to move the retractor during the procedure. The lid retractor comprises an elongated handle which at one end, the gripper end, divides into several projections each terminating in a hook that can be placed over the lower lid to enable the lower lid to be retracted to access lid or eye regions under the lid retractor. The gripper is dimensioned so that the whole eyelid can be pulled down such that several fat compartments under the eyelid can be accessed, visualized, and surgically treated without having to move the lid retractor position.

6 Claims, 2 Drawing Sheets

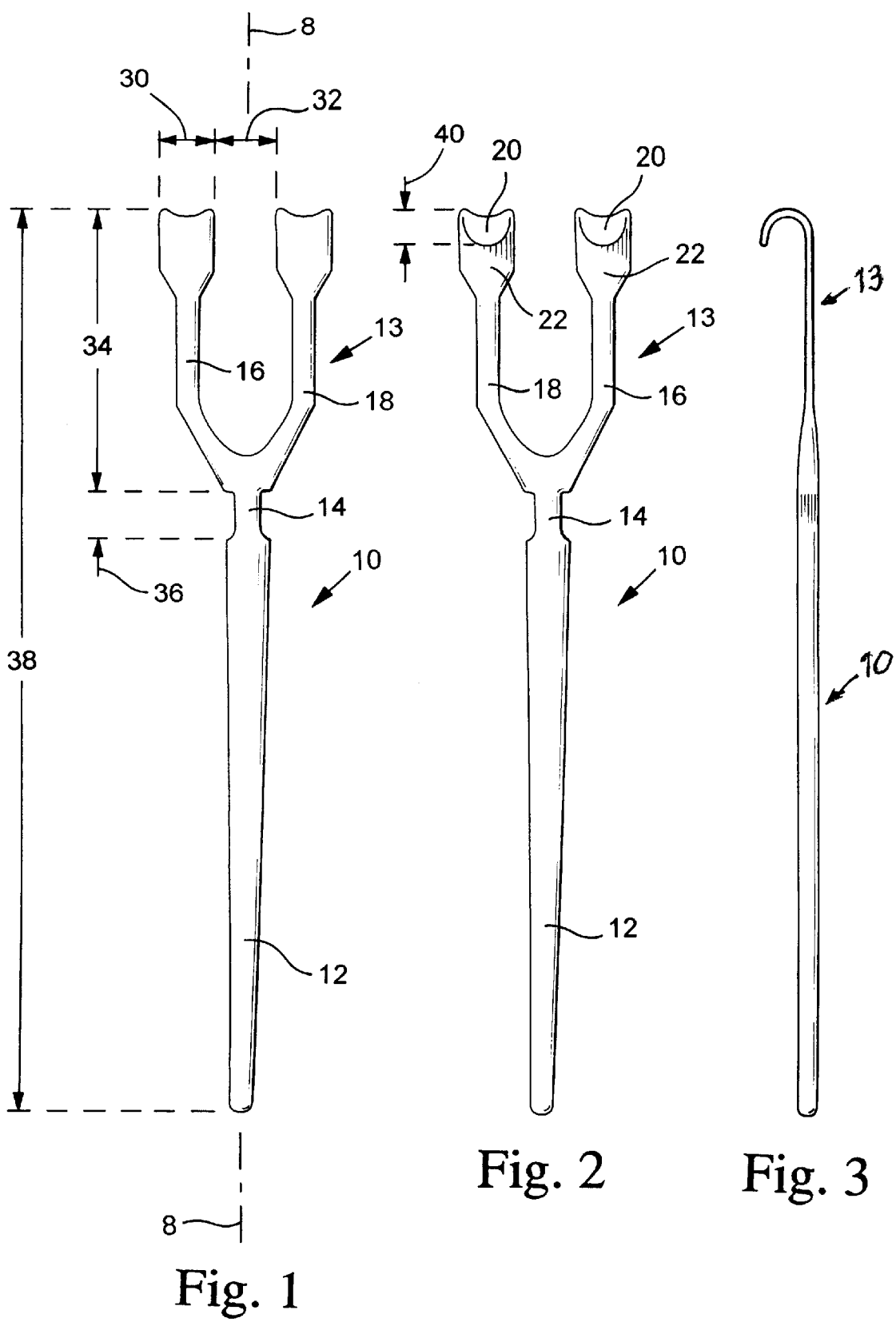

EYELID RETRACTOR FOR ELECTROSURGERY

This invention relates to an eyelid retractor for electrosurgery.

BACKGROUND OF THE INVENTION

Electrosurgery is a common procedure for doctors in all fields, including opthalmology, where it has been used in eyelid procedures where cutting or coagulation is required. One common procedure is known as transconjuntival blepharoplasty, which is the removal of fat pads from the lower lid—in layman terms the removal or reduction of the common bags under the eyes. In this procedure, a lid retractor is applied to the lower lid to pull it down and expose the fat pads inside. One known retractor has a single hook end which can be inserted in a portion of the lower lid to pull down that portion to expose a fat pad underneath. Electrosurgical handpieces are commercially available that will accommodate a wide variety of electrodes shapes and sizes, such as needles, blades, scalpels, balls and wire loops which can be used to excise the fat pad. However, several fat pads are present under the lower lid and to remove the other fat pads requires that the retractor may have to be removed and placed in another opposition over the next fat pad to expose it for excision.

A limitation of this procedure is the additional time spent in having each time to shut off the electrosurgical instrument, move the retractor to a new location over the next fat pad, and activate the instrument to excise that fat pad, and so on.

SUMMARY OF THE INVENTION

An object of the invention is a novel lid retractor for use in electrosurgery on eyelids or portions of the eye under the lid which avoids having to move the retractor during the procedure.

Another object of the invention is a novel lid retractor for use in transconjuntival blepharoplasty electrosurgery on eyelids which avoids having to move the retractor during the procedure.

According to one aspect of the invention, the lid retractor comprises a handle which at one end, the gripper end, divides into several projections each terminating in a hook that can be placed over the lower lid retractor to enable the lower lid retractor to be retracted to access lid or eye regions under the lid retractor.

According to a preferred embodiment of the invention, the gripper end is divided into two substantially parallel arms each of which terminates in a looped over portion that will fit under the typical eyelid of a patient. The arms are separated by a distance approximately equal to or somewhat smaller to the width of a typical fat pad. The total width of the gripper end is approximately equal to the average width of a typical fat pad. As a result, when the gripper is placed on the lower lid to retract same with the two arms located approximately on opposite sides of the middle fat pad, between it and the adjacent fat pads, then all three fat pads can be reached by an electrosurgical electrode without relocating the gripper.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

In the drawings:

FIG. 1 is a top view of one form of lid retractor according to the invention;

FIG. 2 is a bottom view of the lid retractor of FIG. 1;

FIG. 3 is a side view of the lid retractor of FIG. 1;

DETAILED DESCRIPTION OF THE PREFERRED EMBODIMENTS

Figure 4:
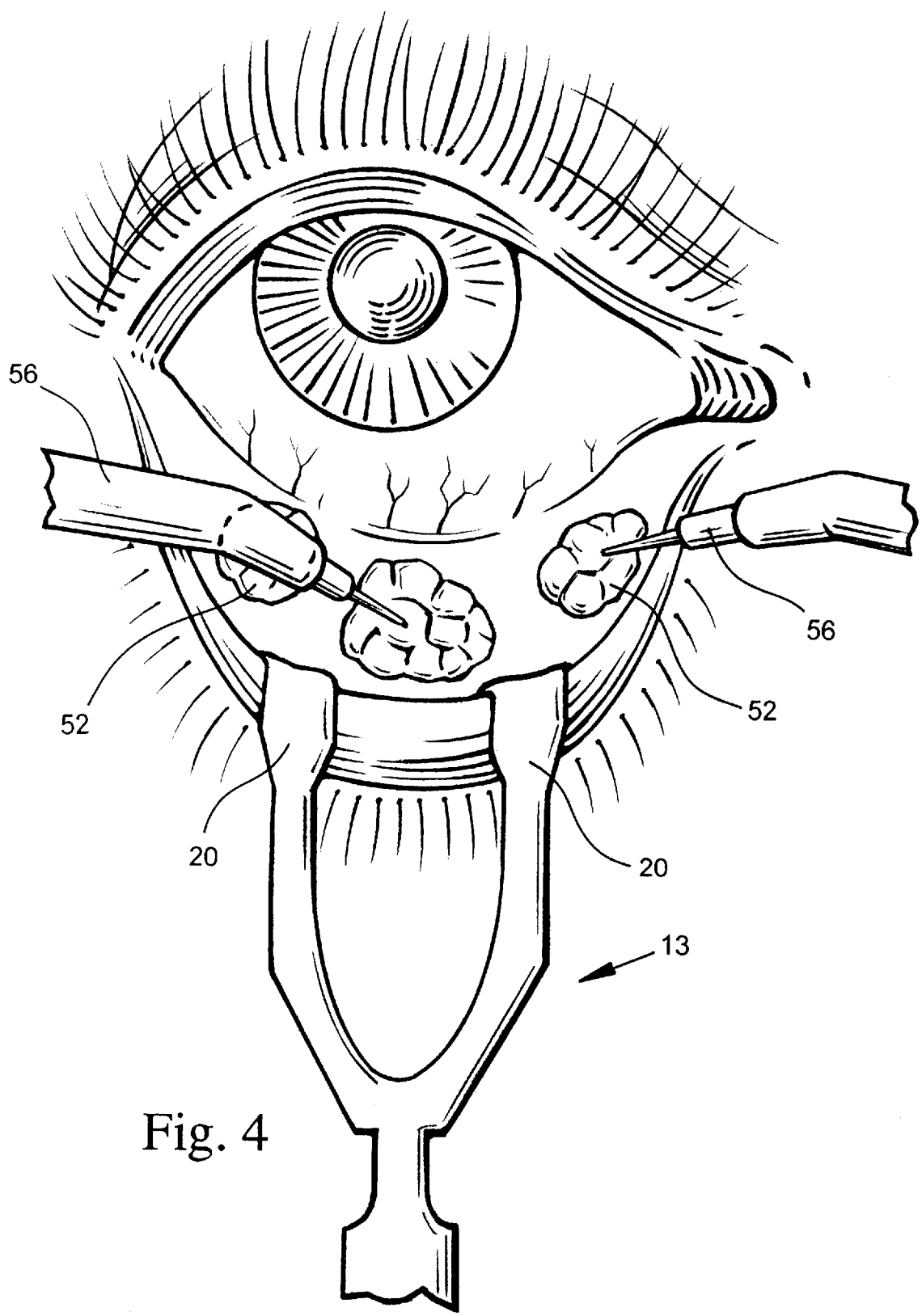
FIG. 4 is a schematic view of the lower lid of a patient with the lid retractor of the invention showing three fat pads underneath and access by an electrosurgical electrode to several of the fat pads.

U.S. Pat. No. 5,984,918 shows a typical electrosurgical handpiece and electrode well known in the art. The present invention is usable with such equipment and many other configurations of handpieces and electrodes as well as with many known forms of electrosurgical generators of RF currents for performing electrosurgery, whose contents are incorporated herein by reference.

The present invention deals with the configuration of an eyelid retractor for use in performing electrosurgical procedures on eyes or eyelids. It is especially useful when employed as a lid retractor for a transconjuntival blepharoplasty procedure using electrosurgery, especially for removing or reducing the size of the typical three fat pads that grow under the lower lid.

Referring to FIGS. 1, 2 and 3, one form of lid retractor 10 according to the invention comprises a single metal body, preferably of sterilizable metal, such as stainless steel or surgical steel, extending in a longitudinal direction symmetrical about a longitudinal axis 8, and comprising a handle 12 from which projects a gripper portion 13. The gripper portion 13 comprises two substantially parallel arms 16, 18 which terminate in folded over or looped portions 20. The arms 16, 18 slightly widen to form the looped portions 20, the narrower section providing increased visibility for the surgeon. The gripper end 13 is connected by a necked-down portion 14 to the handle 12. The longitudinal axis 8 bisects the arms 16, 18, which also extend generally parallel to the axis 8. The whole structure is in one plane except for the two looped portions 20.

The dimensions are important and are as follows. The width 30 of each of the looped portions 20 is between about 0.5–0.9 cm, preferably about 0.8 cm; the width of the spacing 32 between the looped portions 20 is between about 1–1.4 cm, preferably about 1.2 cm; thus the overall width of gripper end 13 is between about 2–3.2 cm, preferably about 2.8 cm; the length 34 of gripper end 13 is between about 3.5–5 cm, preferably about 4.5 cm; the length 36 of the necked-down section 14 is between about 0.4–0.8 cm, preferably about 0.6 cm; the overall length 38 of the lid retractor is between about 12–16 cm, preferably about 14 cm; the length 40 of the looped section 20 is between about 0.4–0.6 cm, preferably about 0.5 cm. The significance of the dimensions is that the loop size fits conveniently over the eyelid into the space underneath and the gripper is wide enough allowing the whole lower lid to be pulled down or retracted gaining access by the surgeon to the entire lower eyelid sufficiently to expose the fat pads for access by the active electrosurgical electrode; the arms 16, 18 and looped ends 20 are separated by a distance approximately equal to or somewhat smaller than the width of a typical fat pad; and the total width of the gripper end is approximately equal to the average width of a typical fat pad. As a result, when the gripper loops 20 are placed on the lower lid to retract same with the two arms located approximately on opposite sides of the middle fat pad, between it and the adjacent fat pads, then all three fat pads can be reached by an electrosurgical electrode without relocating the gripper.

This can be seen in the schematic drawing of FIG. 4, which show the eyelid of a patient pulled down by the lid retractor of the invention exposing three fat pads 52 on the underside of the lid. FIG. 4 illustrates how the needle electrode of an electrosurgical handpiece 56 can separately access the middle and right fat pads 52 for palpitation, incision, or reduction. The left fat pad 52 can be similarly accessed. Thus all three fat compartments can be accessed in all three locations, visualized, and surgically treated without having to change the lid retractor position.

While it is preferred to make the lid retractor of a single piece of metal, it is also possible to mold it as several pieces of different materials. Other variations will be evident to those skilled in the art.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A lid retractor for use in transconjuntival blepharoplasty electrosurgery on eyelids to remove or reduce three laterally spaced fat compartments on the underside of the eyelid, comprising:

a) an elongated body having a handle connected to a gripper end divided into two laterally-spaced projections each terminating in a looped end that can be placed over an eyelid to enable the lid to be retracted to access lid or eye regions under the lid, b) the gripper being dimensioned such that substantially the whole eyelid can be pulled down so that the three laterally spaced fat compartments under the eyelid can be accessed, visualized, and surgically treated without having to change the lid retractor position, c) the looped ends on the two spaced projections being laterally spaced apart a distance such that, when pulling on an eyelid, the looped end positions allow access by an electrosurgical electrode to all three fat compartments without having to change the lid retractor position.

2. A lid retractor for use in an electrosurgical procedure to remove or reduce tissue regions on or under eyelids as claimed in claim 1, wherein the body has a longitudinal axis, and the handle and the two spaced projections extend substantially parallel to each other and are bisected by the longitudinal axis.

3. A lid retractor for use in an electrosurgical procedure to remove or reduce tissue regions on or under eyelids as claimed in claim 2, wherein the width (30) of each of the looped ends (20) is between about 0.5–0.9 cm; the width of the spacing (32) between the looped ends (20) is between about 1–1.4 cm.

4. A lid retractor for use in an electrosurgical procedure to remove or reduce tissue regions on or under eyelids as claimed in claim 2, wherein the width (30) of each of the looped ends (20) is about 0.8 cm; and the width of the spacing (32) between the looped ends (20) is about 1.2 cm.

5. A lid retractor for use in an electrosurgical procedure to remove or reduce tissue regions on or under eyelids as claimed in claim 3, wherein a portion (14) of the handle adjacent the two projections is necked-down, the overall width of gripper end (13) is between about 2–3.2 cm; the length (34) of gripper end (13) is between about 3.5–5 cm; the length (36) of the necked-down section (14) is between about 0.4–0.8 cm; the overall length (38) of the lid retractor is between about 12–16 cm; and the length (40) of the looped ends (20) is between about 0.4–0.6 cm.

6. A lid retractor for use in an electrosurgical procedure to remove or reduce tissue regions on or under eyelids as claimed in claim 5, wherein the overall width of gripper end (13) is about 2.8 cm; the length (34) of gripper end (13) is about 4.5 cm; the length (36) of the necked-down section (14) is about 0.6 cm; the overall length (38) of the lid retractor is about 14 cm; and the length (40) of the looped ends (20) is about 0.5 cm.

* * * * *